(12) United States Patent
Divi et al.

(10) Patent No.: US 8,586,792 B2
(45) Date of Patent: Nov. 19, 2013

(54) PROCESS FOR THE PREPARATION OF 4-IODO-3-NITROBENZAMIDE

(75) Inventors: Murali Krishna Prasad Divi, Hyderabad (IN); Mysore Aswatha Narayana Rao, Hyderabad (IN); Venkataramana Rajuri, Hyderabad (IN)

(73) Assignee: Divi's Laboratories Ltd. (IN)

( * ) Notice: Subject to any disclaimer, the term of this patent is extended or adjusted under 35 U.S.C. 154(b) by 155 days.

(21) Appl. No.: 13/416,454

(22) Filed: Mar. 9, 2012

(65) Prior Publication Data

US 2013/0172618 A1 Jul. 4, 2013

(30) Foreign Application Priority Data

Dec. 28, 2011 (IN) .......................... 4626/CHE/2011

(51) Int. Cl.
*C07C 231/02* (2006.01)
(52) U.S. Cl.
USPC ......................................................... 564/134

(58) Field of Classification Search
USPC ......................................................... 564/134
See application file for complete search history.

(56) References Cited

U.S. PATENT DOCUMENTS

| 5,464,871 A | 11/1995 | Kun et al. |
| 5,877,185 A | 3/1999 | Kun et al. |
| 2007/0135485 A1 | 6/2007 | Gillig et al. |
| 2011/0207767 A1 | 8/2011 | Beusker et al. |

OTHER PUBLICATIONS

Cyrille Monnereau, et al. Synthesis of new crosslinkable co-polymers containing a push-pull zinc porphyrin for non-linear optical applications, Tetrahedron 61 (2005) 10113-10121.
John I. Trujillo, et al. Facile Esterification of sulfonic Acids and Carboxylic Acids with Triethylorthoacetate, Tetrahedron Letters, vol. 34, No. 46, pp. 7355-7358, 1993.
Louis Storace, et al. An Efficient Large-Scale Process for the Human Leukocyte Elastase Inhibitor, DMP 777, Organic Process Research & Development 2002, 6, 54-63.

*Primary Examiner* — Shailendra Kumar
(74) *Attorney, Agent, or Firm* — Caesar, Rivise, Bernstein, Cohen & Pokotilow, Ltd.

(57) ABSTRACT

A process for the preparation of 4-iodo-3-nitrobenzamide free from the impurities formed due to nucleophilic substitution of the labile iodo group is disclosed.

4 Claims, No Drawings

PROCESS FOR THE PREPARATION OF 4-IODO-3-NITROBENZAMIDE

CROSS-REFERENCE TO RELATED APPLICATION

This application claims priority from India Application 4626/CHE/2011, filed Dec. 28, 2011, entitled A PROCESS FOR THE PREPARATION OF 4-IODO-3-NITROBENZAMIDE of which the following is a specification, which application is assigned to the same assignee as this application and whose disclosure is incorporated by reference herein.

FIELD OF THE INVENTION

The present invention describes a process for 4-iodo-3-nitrobenzamide (Iniparib), a molecule currently in clinical trials for the treatment of breast cancer.

BACKGROUND OF THE INVENTION

Iniparib, 4-iodo-3-nitrobenzamide (Formula 1), is undergoing clinical trials for the treatment of certain types of breast cancer.

Formula 1

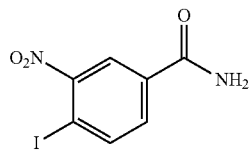

Its action is attributed to inhibition of poly-ADP-ribose-polymerase (PARP).

Its preparation is described in U.S. Pat. Nos. 5,464,871 and 5,877,185. The method described in the '871 and '185 patents, involves reacting 4-iodo-3-nitrobenzoic acid with thionyl chloride in dimethylformamide (DMF) to obtain the acid chloride in situ, followed by reaction with ammonium hydroxide (Scheme-1), with about 48.8% crude yield. After recrystallization from acetonitrile solvent, a yield of only 40.5% was obtained. The recrystallized product showed signals for acetonitrile in 1H-NMR. The integration of the acetonitrile signal indicates approximately one molecule of acetonitrile per three molecules of 4-iodo-3-nitrobenzamide.

This was further confirmed by elemental analysis data. Acetonitrile is not a safe chemical since it metabolizes to give highly toxic hydrogen cyanide.

Scheme 1

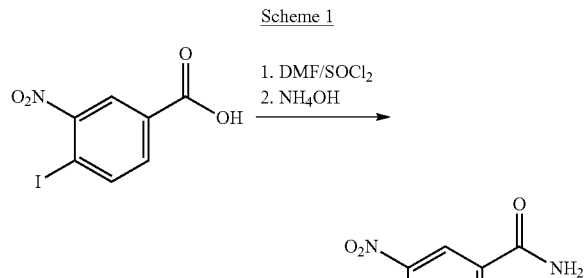

Another major problem encountered while preparing 4-iodo-3-nitrobenzamide using the above method is the formation of 4-chloro-3-nitrobenzamide as an impurity. During the reaction with thionyl chloride, a nucleophilic aromatic substitution of 4-iodo with chloro to give 4-chloro-3-nitrobenzamide was observed (Scheme 2) as a side reaction.

Scheme 2

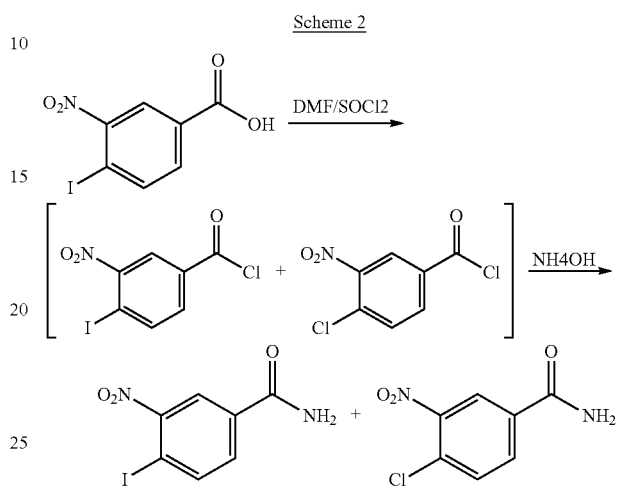

The iodo group is activated for such a nucleophilic substitution because of the presence of a nitro group at the ortho position in the benzene ring. Further, the reaction is facilitated by the use of DMF, an aprotic solvent. The authors observed about 2-5% of the chloro impurity (U.S. '871 and '185). Even after repeated crystallizations, the impurity could not be removed completely but resulted in significant loss in yield of the required compound.

Thus, the synthetic process described in the prior art suffers from:

1. low yields;
2. presence of residual acetonitrile in the final product; and
3. formation of 4-chloro-3-nitrobenzamide as an impurity.

SUMMARY OF THE INVENTION

Since the chloro impurity is formed because of nucleophilic substitution and is promoted by DMF, other non-aprotic solvents were tried, but without success. Next, thionyl bromide was used in place of thionyl chloride, hoping that it would prevent the substitution of the iodo group, as the bromo group is bulky and less nucleophilic. However, the corresponding bromo derivative was obtained as an impurity, albeit in lesser quantity (<1%). Next, the possibility of preparing an amide through an ester was explored (Scheme 3).

Scheme 3

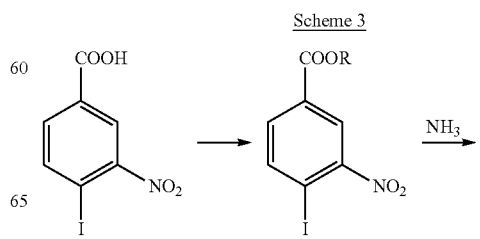

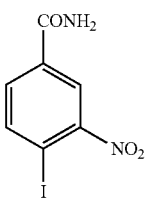

The preparation of an ester generally involves the use of HCl, thionyl chloride, etc. as a catalyst. Such 'chloro' catalysts may again promote nucleophilic substitution. Hence, these were avoided and other catalysts were examined. US patent application, US 2011/0207767 A1 reports the preparation of 4-iodo-3-nitrobenzoic acid ethyl ester by reacting 4-iodo-3-nitrobenzoic acid and ethanol using dicyclohexylcarbodimide (DCC) as a catalyst and N,N-dimethylaminopyridine (DMAP) as a base. DCC and DMAP are expensive agents. Often the dicyclohexyl urea formed during the reaction is difficult to remove and contaminates the product. Further, DCC is a skin sensitizer and generally avoided on an industrial scale (*Org. Process Res. Dev.* 2002, 6, 54-63). Preparation of the methyl ester of 4-iodo-3-nitrobenzoic acid with 77% yield, using sulfuric acid as catalyst, is described in U.S. 2007/0135485 A1 (now abandoned). We have modified the procedure and obtained 85% yield. While exploring other esterification methods, which do not involve a nucleophile, we found that trimethyl orthoacetate is an excellent agent for the preparation of methyl ester (Scheme 4).

Scheme 4

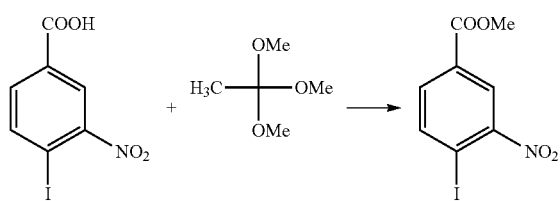

Trimethyl orthoacetate esterifies by direct O-alkylation of carboxylate (*Tetrahedron Letters*, 34, 1993, 7355-7358). Because of this unique mechanism, impurities arising from nucleophilic substitution are not formed. Further an almost quantitative yield (>99%) is obtained. Another advantage is that the reaction can be conducted without any solvent. In the next reaction, the ester is reacted with ammonia at room temperature to obtain the amide, 4-iodo-3-nitrobenzamide in good yield (95% yield, 98% HPLC; after crystallization 80% yield, 99.8% HPLC).

In another embodiment, the present invention provides a new crystallization method using methanol-water and avoids toxic acetonitrile used in the prior art. The new crystallization method gives a highly pure compound (>99.5%).

DETAILED DESCRIPTION OF THE INVENTION

According to the present invention, there is provided a process for the preparation of 4-iodo-3-nitrobenzamide, which comprises:
a) converting 4-iodo-3-nitrobenzoic acid to its methyl ester; and
b) reacting the obtained alkyl ester with ammonia to give 4-iodo-3-nitrobenzamide.

The required starting material, 4-iodo-3-nitrobenzoic acid, can be prepared as described in *Tetrahedron*, 61, 2005, 10113-10121, or by any other suitable method. The conversion of 4-iodo-3-nitrobenzoic acid to its methyl ester using sulfuric acid and methanol is described in U.S. 2007/0135485 A1 (section [0255], page 30). The method involves reacting a methanolic solution of 4-iodo-3-nitrobenzoic acid with sulfuric acid, neutralizing the acid with sodium bicarbonate, removal of methanol, diluting with water and extracting with diethyl ether, to obtain an oily product, which was subjected to chromatography to get 4-iodo-3-nitro benzoic methyl ester as a solid in 77% yield. Diethyl ether is not a suitable solvent on an industrial scale because of its high inflammability. Also column chromatography for purification in large scale is not desirable. Hence, we have modified the reported procedure. We have found that methyl tert-butyl ether (MTBE) is a better solvent for extraction which gives the product as a solid directly without any need for chromatographic purification (98.5% HPLC) and in high yield (85%).

We have also found an alternative, more efficient and simple method for esterification using trimethyl orthoacetate. The method involves dissolving 4-iodo-3-nitrobenzoic acid in trimethyl orthoacetate and refluxing the solution for 15 hours. Removal of the solvent under reduced pressure, gives 4-iodo-3-nitro benzoic methyl ester as a solid in almost quantitative yield (98%, 97% HPLC). It contains about 1.5% starting acid. Since the residual starting acid does not interfere in the next step, the material can be taken directly for the next stage. However, if required, the material can be further purified by crystallization from methanol and water with little loss of yield (95% Y, 98.3% HPLC).

In general, an ester can be converted to its amide by treating with ammonia. Using aqueous ammonia for this purpose resulted in hydrolysis of the ester. In a preferred embodiment of the present method, 4-iodo-3-nitrobenzamide can be prepared by dissolving 4-iodo-3-nitrobenzoic acid methyl ester in a suitable solvent and treating the solution with anhydrous ammonia gas. The suitable solvents for the reaction are methanol, ethanol, isopropanol, acetone and methyl tert-butyl ether. These solvents have the ability to dissolve ammonia in high concentration. The preferred solvent is methanol. The starting ester is dissolved in methanol and ammonia is passed into the solution. Dissolution of ammonia in methanol is an exothermic reaction. Hence initial cooling to −10(±2)° C. is preferred. At this temperature some amount of ester precipitates. However, on passing ammonia, it gets dissolved and results in a clear solution. The solution is saturated with ammonia and kept at ambient temperature in a properly closed container. Monitoring by TLC showed that the reaction is completed in three days. Although most of the conversion takes place in two days, a small amount (5-10%) of the starting material may still be present. When the reaction is conducted in an autoclave under pressure, formation of impurities was observed. Removal of solvent under reduced pressure gives an amide as a yellow solid (95% yield, 98% HPLC). It is further crystallized from hot methanol and water. For crystallization, the amide is dissolved in hot methanol at about 55° C. While the mixture is still hot, water is added and the precipitate formed is filtered. A highly pure (>99.5%) product is obtained. The 1H-NMR shows no signals for methanol. This is an important advantage over the prior art, where the final compound was found to contain acetonitrile, a toxic solvent used during crystallization.

The embodiments of the present invention are illustrated in the following examples, which are not intended in any way to limit the scope of the invention. One skilled in the art can easily modify the details to suit the inputs and desired outcomes without affecting the present invention.

EXAMPLES

Chemical purity was determined using HPLC on an Inertsil ODS-3V column at 260 nm with 0.1% formic acid in $H_2O$ and 0.1% formic acid in acetonitrile as mobile phase.

Example 1

Preparation of 4-iodo-3-nitrobenzoic Acid Methyl Ester Using Methanol/Sulfuric Acid To a solution of 4-iodo-3-nitrobenzoic acid (3 g, 10 mmol) in methanol (30 ml) cooled to 0° C., sulfuric acid (3.4 g, 34.6 mmol) is added slowly. The reaction mixture is warmed to room temperature and then refluxed (~70° C.) for 8 hours. After cooling, the reaction mixture is neutralized with solid $NaHCO_3$ and the salts are filtered. The filtrate is evaporated under reduced pressure. To the residue obtained, water (30 ml) is added and the mixture extracted with MTBE (30 ml×2). The combined organic phase is washed with brine, dried using anhydrous sodium sulfate and filtered. After evaporating the solvent under reduced pressure, 4-iodo-3-nitro-benzoic acid methyl ester is obtained as a yellow solid (2.67 g, 85% yield, 98% HPLC).

Example 2

Preparation of 4-iodo-3-nitrobenzoic Acid Methyl Ester Using Trimethyl Orthoacetate A solution of 4-iodo-3-nitrobenzoic acid (3 g, 10 mmol) in trimethyl orthoacetate (30 ml) is refluxed (~110° C.) for 15 hours and then solvent is evaporated under reduced pressure. The 4-iodo-3-nitrobenzoic acid methyl ester is obtained as a yellow solid (3.11 g, 99% yield, 97.5% HPLC).

Example 3

Preparation of 4-iodo-3-nitrobenzamide

A solution of 4-iodo-3-nitrobenzoic acid methyl ester (2.0 g, 6.5 mmol) in methanol (80 ml) is cooled to −15° C. To the solution, ammonia gas (about 1.02 g, 0.06 mol) is passed till saturation. The solution is kept at room temperature (25±2° C.) for 3 days. The solvent is then evaporated under reduced pressure to obtain 4-iodo-3-nitrobenzamide as an yellow solid (95% yield, 98% HPLC). The solid (1 g) is added to methanol (10 ml) and heated to 55° C. to get a clear solution. While the solution is hot, water (35 ml) is added and the precipitate so formed is filtered to obtain pure 4-iodo-3-nitrobenzamide.

$^1$H-NMR spectrum: DMSO-$d_6$: δ 7.74 (brs, $NH_2$), 7.86 (dd, Ar—H), 8.24 (d, Ar—H), 8.70 (d, Ar—H). $^{13}$C-NMR spectrum: DMSO-$d_6$: δ 91.76, 123.63, 132.03, 135.36, 141.49, 153.15, and 165.19. Yield: 1.52 g (80.2%), 99.6-99.8% HPLC.

We claim:

1. A process for the preparation of 4-iodo-3-nitrobenzamide (Iniparib), which comprises:
    a) converting 4-iodo-3-nitrobenzoic acid to its methyl ester, wherein the methyl ester is prepared by reacting 4-iodo-3-nitrobenzoic acid with trimethyl orthoacetate,
    b) reacting the methyl ester with ammonia to give 4-iodo-3-nitrobenzamide, and
    c) crystallization of 4-iodo-3-nitrobenzamide using a mixture of alcohol and water.

2. The process according to claim 1, step-b, wherein the methyl ester is treated with ammonia gas in a non-aqueous polar solvent.

3. The process according to claim 2, wherein the non-aqueous polar solvent used is methanol.

4. The process according to claim 1, step-c, wherein the alcohol used is methanol.

* * * * *